United States Patent [19]
Peck

[11] 4,379,881
[45] Apr. 12, 1983

[54] ADHESIVE SUITABLE FOR APPLICATION TO SKIN

[75] Inventor: Roger F. Peck, Stansted Mountfitchet, England

[73] Assignee: Smith and Nephew Associated Companies Limited, England

[21] Appl. No.: 240,987

[22] Filed: Mar. 5, 1981

[30] Foreign Application Priority Data

Mar. 5, 1980 [GB] United Kingdom ............... 8007410

[51] Int. Cl.³ ............................................. C08K 5/10
[52] U.S. Cl. ................................. 524/315; 524/365; 524/561; 526/317; 526/328
[58] Field of Search ................ 260/31.2 R, 328; 526/328, 317; 524/315, 365, 561

[56] References Cited

U.S. PATENT DOCUMENTS

| | | | |
|---|---|---|---|
| 3,535,295 | 10/1970 | Davis et al. | 260/80.8 |
| 3,547,950 | 12/1970 | Gander | 260/33.2 |
| 3,563,953 | 2/1971 | Lehmann et al. | 260/63 |
| 3,738,971 | 6/1973 | Coffman | 260/80.73 |
| 3,971,766 | 7/1976 | Ono et al. | 526/317 |
| 3,998,997 | 12/1976 | Mowdood et al. | 526/271 |
| 4,144,208 | 3/1979 | Fuchs et al. | 260/27 R |

Primary Examiner—Joseph L. Schofer
Assistant Examiner—Bernard Lipman
Attorney, Agent, or Firm—Jacobs & Jacobs

[57] ABSTRACT

An adhesive polyacrylate which has a K value of 90 to 110 and contains 16% to 62% of n-butyl acrylate residues, 80% to 34% of 2-ethylhexyl acrylate residues and 4% to 10% acrylic acid residues, solutions thereof, surgical adhesive sheet materials coated therewith and their preparation are described.

9 Claims, No Drawings

ADHESIVE SUITABLE FOR APPLICATION TO SKIN

The present invention relates to a pressure sensitive adhesive suitable for application to skin, for example for adhering first aid dressings or the like to skin.

It has proved very difficult to provide an adhesive for first aid dressings or the like that adheres firmly under dry and moist conditions but does not damage skin when the dressing is removed. A suitable adhesive has now been discovered.

The present invention provides an adhesive polyacrylate which has a K value of 90 to 110 and contains 16% to 62% of n-butylacrylate residues, 80% to 34% of 2-ethylhexyl acrylate residues and 4% to 10% of acrylic acid residues.

All % terms herein are expressed on wt/wt basis.

Very desirably the polymer contains 34% to 62% n-butyl acrylate residues. Very desirably the polymer contains 62% to 34% of 2-ethylhexyl acrylate residues. Very desirably the polymer contains 4% to 8% of acrylic acid residues.

More suitably the polymer contains 45% to 55% n-butyl acrylate residues. More suitably the polymer contains 45% to 55% of 2-ethylhexylacrylate residues. More suitably the polymer contains 5% to 7% acrylic acid residues. Preferably the polymer contains 47% n-butyl acrylate residues. Preferably the polymer contains 47% 2-ethylhexyl acrylate residues. Preferably the polymer contains 6% acrylic acid residues.

The adhesive polymer of this invention will not have a high degree of crosslinking; that is, the polymer is effectively linear. This results in the adhesive polymer being capable of being dissolved in solvent even after tunnel spreading.

The K value of the polymer of this invention will be within the range 90 to 110, most suitably 91 to 106 and is preferably within the range 95 to 105 and most preferably within the range 96 to 100. (K values may be determined by the published method of DIN 53726). (K values of 90, 95, 105 and 110 are equivalent to inherent viscosities of 1.7, 1,9, 2.5 and 3.0 dl/g). The polymers of this invention with these K-values have acceptable cohesive strength and acceptable wet-stick. These desirable properties are particularly apparent when the adhesive polymer has a wider molecular weight distribution.

In another aspect the invention provides a solution in acetone or ethyl acetate of an adhesive polyacrylate wherein the solution contains 20 to 45% of adhesive polyacrylate.

In general the polymer of this invention is provided in the form of a solution such as acetone, ethyl acetate or the like. A 20 to 45% solution in acetone is a favoured form, for example a 30 to 40% solution.

In another embodiment the invention provides a surgical adhesive sheet material wherein the adhesive comprises an adhesive polyacrylate. Favoured surgical adhesive sheet materials are moisture vapour permeable.

Preferred surgical adhesive sheet materials will have a moisture vapour transmission rate of not less than 300 g/m$^2$/24 hrs/37.5° C. at 100% to 10% relative humidity difference.

The adhesive coating of the surgical sheet material can be discontinuous or continuous. Preferred adhesive coatings are continuous. Continuous coatings will normally have a weight of 10 to 300 g/m$^2$. Apt continuous coatings have a weight of 15 g/m$^2$ to 250 g/m$^2$. Discontinuous adhesive coatings can be porous or in a pattern which leaves areas of the sheet material free from adhesive for example in a pattern as disclosed in British Pat. No. 810635.

The polymers of this invention may be prepared by free radical catalysed polymerisation in acetone or like organic solvent such as acetone toluene mixtures or ethyl acetate. Suitable catalysts for use include peroxides such as benzoyl peroxide or other initiators such as azobisisobutyronitrile. In general moderately elevated temperatures such as 50° to 65° C. are employed, for example at the reflux temperature of an acetone solution.

The adhesive of the invention may contain an antioxidant, for example by up to 1% of the dry adhesive. A favoured antioxidant is known as Permanax W.S.L. from Vulnax International Limited. Permanax W.S.L. is an alpha-1-methyl cyclohexyl derivative of selected xylenols.

The adhesive of this invention may be used to coat fabrics, porous polyvinylchloride film, polyurethane film, integral nets and the like in order to produce first aid dressings by conventional spreading techniques such as transfer spreading or direct spreading.

The following Examples illustrate the invention.

EXAMPLE 1

Preparation of Acrylic Adhesive Formulation

Reagents:
- Glacial Acrylic Acid: 75.2 g (75.2 cm$^3$)
- 2-ethylhexylacrylate: 589 g (665 cm$^3$)
- n-butylacrylate: 589 g (665 cm$^3$)
- Benzoyl peroxide: 0.9 g dissolved in 30 cm$^3$ acetone
- Acetone: 1412 g (1790 cm$^3$)

Apparatus: 5l resin flask fitted with an anchor type stirrer, condenser thermocouple holder, nitrogen inlet and dropping funnel; assembled on a steam bath.

Procedure: 80% of the acetone together with ⅓ of the monomers were charged into the resin flask and purged with nitrogen for 10 minutes. Steam was turned on contents heated to gentle reflux. 5 cm$^3$ of the benzoyl peroxide catalyst was added and the reactants allowed to react for 3 hours. The rest of the reactants were charged to the pot as shown in the table below.

| Rectants | Reaction time (Hrs) | Pot Temp. (°C.) |
|---|---|---|
| 1/3M + 1/6C | 0–3 | 60°–57° |
| +1/6M + 1/6C | 3–5 | 58.5° |
| +1/6M + 1/6C | 5–6¾ | 60° |
| +1/6M + 1/6C | 6¾–8¼ | 60° |
| +1/6M + 1/6C | 8¼–9¼ | 60° |

On complete addition of monomers, the 5l resin flask was removed from the steam bath and was assembled on a constant temperature bath kept at 60° C. (±1). 20% of the acetone and the remainder of the catalyst (1/6) was added to the pot and the reaction mixture was allowed to react for a further 14¾ hours i.e. total reaction time=24 hours.

Assay: (Residual monomer content less than 1%; K value=100; the cohesive strength of the adhesive was sufficient to prevent cohesive failure on skin under wet conditions).

EXAMPLE 2

A further amount of acetone was added to the mixture of Example 1 to give a solution containing 33% of the adhesive polyacrylate.

EXAMPLE 3

The adhesive of Example 2 was coated onto Estane 5714F (B. F. Goodrich) polyurethane film (weight 28g/m$^2$) supported on a release paper (Steralease 15 from Sterling Coated Papers Ltd.) by a conventional blade over flat bed coating unit to give a continuous coating (dry weight 30 g/m$^3$). The adhesive coated polyurethane film had a moisture vapour transmission rate of 755 g/m$^2$/24 hrs/at 37.5° C. at 100% to 10% relative humidity difference.

The adhesive coated polyurethane film was converted into wound dressings and surgical drapes.

EXAMPLE 4

The adhesive of Example 2 was coated onto a B.P.C. elastic transverse stretch woven cotton cloth by conventional blade over flat bed coating unit to give a continuous coating (dry weight 90 g/m$^2$). The adhesive coated cloth had a moisture vapour transmission rate of 585 g/m$^2$/24 hrs/at 37.5° C. at 100% to 10% relative humidity difference.

The adhesive coated elastic cloth was converted into first aid dressings.

EXAMPLE 5

The adhesive of Example 2 was coated onto a release paper (Steralease 77 from Sterling Coated Papers Ltd.) and transferred to a 250 micron microporous PVC sheet by a conventional transfer lamination process to give a continuous coating (dry weight 40–50 g/m$^2$). The adhesive coated microporous PVC sheet had a moisture vapour transmission rate of 730 g/m$^2$/24 hrs/at 37.5° C. at 100% to 10% relative humidity difference.

The adhesive coated microporous PVC sheet was converted into first aid dressings.

EXAMPLE 6

The adhesive of Example 2 was spread onto a 250 micron microporous PVC sheet (dry weight 40 g/m$^2$) in a pattern of lines to leave unspread areas of diamond shape using a grooved roller according to the method described in British Pat. No. 819,635. The roller had two sets of 2.5 per cm intersecting parallel groove lines at 45° to the roller axis and a pattern of square diamond raised areas.

The adhesive coated microporous PVC had a moisture vapour transmission rate of 2758 g/m$^2$/24 hrs/at 37.5° C./at 100% to 10% relative humidity difference. The adhesive coated microporous PVC sheet was converted into first aid dressings.

EXAMPLE 7

The adhesive of Example 2 was transfer coated in a similar manner to Example 4 onto the net of Example 1 of British Patent Specification No. 1,531,715 to give a continuous coating (dry weight 47g/m$^2$). The adhesive coated net has a moisture vapour transmission rate of 417g/m$^2$/24 hrs/at 37.5° C. at 100% to 10% relative humidity difference. The adhesive coated net was converted into first aid dressings.

DESCRIPTION

Dressings of Examples 4, 5, 6 and 7 were clinically tested by adhering the dressing on the index finger of volunteers for a period of up to 48 hours. All the dressings showed satisfactory adhesion to skin.

What we claim is:

1. An adhesive linear polyacrylate which has a K value of 90 to 110 and consists of 34% to 62% of n-butyl acrylate residues 62% to 34% of 2-ethylhexyl acrylate residues and 4% to 8% of acrylic acid residues.

2. An adhesive polyacrylate according to claim 1 which contains 45% to 55% of n-butyl acrylate residues, 45% to 55% of 2-ethylhexyl acrylate residues and 5% to 7% of acrylic acid residues.

3. An adhesive polyacrylate according to claim 2 which contains 47% n-butyl acrylate residues, 47% 2-ethylhexyl acrylate residues and 6% acrylic acid residues.

4. A solution in acetone or ethyl acetate of an adhesive polyacrylate according to claim 1 wherein the solution contains 20% to 45% of adhesive polyacrylate.

5. A process for the preparation of an adhesive polyacrylate according to claim 1 which comprises copolymerising a mixture of n-butyl acrylate, 2-ethylhexyl acrylate and acrylic acid in the desired propostions by free radical polymerisation in an organic solvent and thereafter optionally removing the solvent.

6. A solution in acetone which contains 30% to 40% of an adhesive linear polyacrylate which has a K value of 90 to 110 and consists of 45% to 55% n-butyl acrylate residues, 45% to 55% of 2-ethylhexyl acrylate residues and 5% to 7% of acrylic acid residues.

7. An adhesive polyacrylate according to claim 1 wherein the K value is 91 to 106.

8. An adhesive polyacrylate according to claim 1 wherein the K value is 95 to 105.

9. An adhesive polyacrylate according to claim 1 wherein the K value is 96 to 100.

* * * * *